(12) United States Patent
Hardy

(10) Patent No.: US 7,206,717 B2
(45) Date of Patent: Apr. 17, 2007

(54) SENSOR ALIGNMENT METHOD FOR 3D MEASUREMENT SYSTEMS

(75) Inventor: Kevin George Hardy, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 1070 days.

(21) Appl. No.: 10/063,787

(22) Filed: May 13, 2002

(65) Prior Publication Data

US 2003/0210406 A1 Nov. 13, 2003

(51) Int. Cl.
  *G01C 9/00* (2006.01)
(52) U.S. Cl. ...................................... 702/152
(58) Field of Classification Search .................. 702/152
  See application file for complete search history.

(56) References Cited

U.S. PATENT DOCUMENTS 4,653,104 A * 3/1987 Tamura ...................... 382/154
6,024,449 A * 2/2000 Smith .......................... 351/212
6,163,376 A * 12/2000 Nomura et al. .............. 356/401
6,539,638 B1 * 4/2003 Pelletier ....................... 33/290
6,727,979 B2 * 4/2004 Kobayashi et al. ........... 355/53
2003/0067537 A1 * 4/2003 Myers .......................... 348/47

* cited by examiner

*Primary Examiner*—Michael Nghiem
*Assistant Examiner*—Demetrius Pretlow
(74) *Attorney, Agent, or Firm*—Fletcher Yoder

(57) ABSTRACT

A method of set up and alignment of a structured light system for light gauge testing of an object (A). An initial alignment is made of the system with a test specimen mounted in a fixture. Light stripes (L1–Ln) generated by the structured light system are projected onto the part and images of the reflections are captured by cameras and evaluated to determine the characteristics of each stripe over a section of the specimen. If features are not within predetermined limits, or if intensity distribution is not Gaussian, the test setup is adjusted and the process repeated. An imaging system used in the test is also checked to verify the quality of the images captured and processed. If necessary, viewing windows, polarizers, and other electrical components are evaluated to insure the imaging system is properly focused.

27 Claims, 2 Drawing Sheets

SENSOR ALIGNMENT METHOD FOR 3D MEASUREMENT SYSTEMS

BACKGROUND OF INVENTION

This invention relates to the measurement of physical characteristics of three dimensional (3D) objects such as turbine blades used in aircraft engines and the like, and more particularly, to a method for checking the alignment of a structured light 3D measurement system employed in such testing using line video data and interferometry tools.

In testing of objects such as turbine blades which have a complex outer surface or contour, it is advantageous to employ a light gauging testing methodology rather than using conventional hard gauging techniques. This involves the use of a structured light system such as the 4DI light system available from Intelligent Automation. To obtain the most accurate test data for evaluating a part to determine its acceptability, the structured light system employed must be properly setup and aligned. Minor variations in the width of lines of light projected by the structured light system onto the object, for example, can significantly effect the test results and cause an otherwise acceptable part to be rejected, or an unacceptable part to be approved. Similar problems occur if optical windows within the system are not properly aligned.

Previously, alignment of the structured light system to a part under test was accomplished manually by a technician, with the technician visually determining when alignment was proper. The present invention is directed to a test setup methodology by which optical windows are checked to determine when optical windows are correctly aligned. The lines projected by the structured light system are also tested to insure that they are consistent and fall within the specifications necessary to obtain valid test data.

SUMMARY OF INVENTION

Briefly stated, the present invention is directed to a method of setting up and aligning a structured light system for testing an object using light gauging. The method involves making an initial alignment of the system with a test specimen mounted in or on a test fixture. A series of light stripes generated by the structured light system are then projected onto the specimen. Images of the light stripes reflected from predetermined sections of the test specimen are captured, processed, and reviewed to determine their quality. Among the characteristics of the reflected light stripes reviewed are the width (in pixels) of the stripe along the length of the various sections, and the distribution of the light's intensity. If the pixel width is not within predetermined limits, or if the intensity distribution is not Gaussian, then the test setup is realigned and the process repeated.

In addition to aligning the structured light system with the test fixture, the imaging system is also tested to verify the quality of the images captured and processed. If the shape and position of the lines projected onto a section changes along the length of the section, this is indicative that the viewing system is not properly focused. In addition, the quality of the image is also reviewed. If necessary, the imaging system is refocused by adjusting the various viewing windows and filters comprising the system and another evaluation is made.

Finally, the temperature and humidity of the test facility is controlled to provide an optimal testing environment in which performance of the various testing components is not effected by extremes of either.

The foregoing and other objects, features, and advantages of the invention as well as presently preferred embodiments thereof will become more apparent from the reading of the following description in connection with the accompanying drawings.

BRIEF DESCRIPTION OF DRAWINGS

In the accompanying drawings which form part of the specification.

Corresponding reference numerals indicate corresponding parts throughout the several figures of the drawings.

DETAILED DESCRIPTION

The following detailed description illustrates the invention by way of example and not by way of limitation. The description clearly enables one skilled in the art to make and use the invention, describes several embodiments, adaptations, variations, alternatives, and uses of the invention, including what is presently believed to be the best mode of carrying out the invention.

Figure 1:
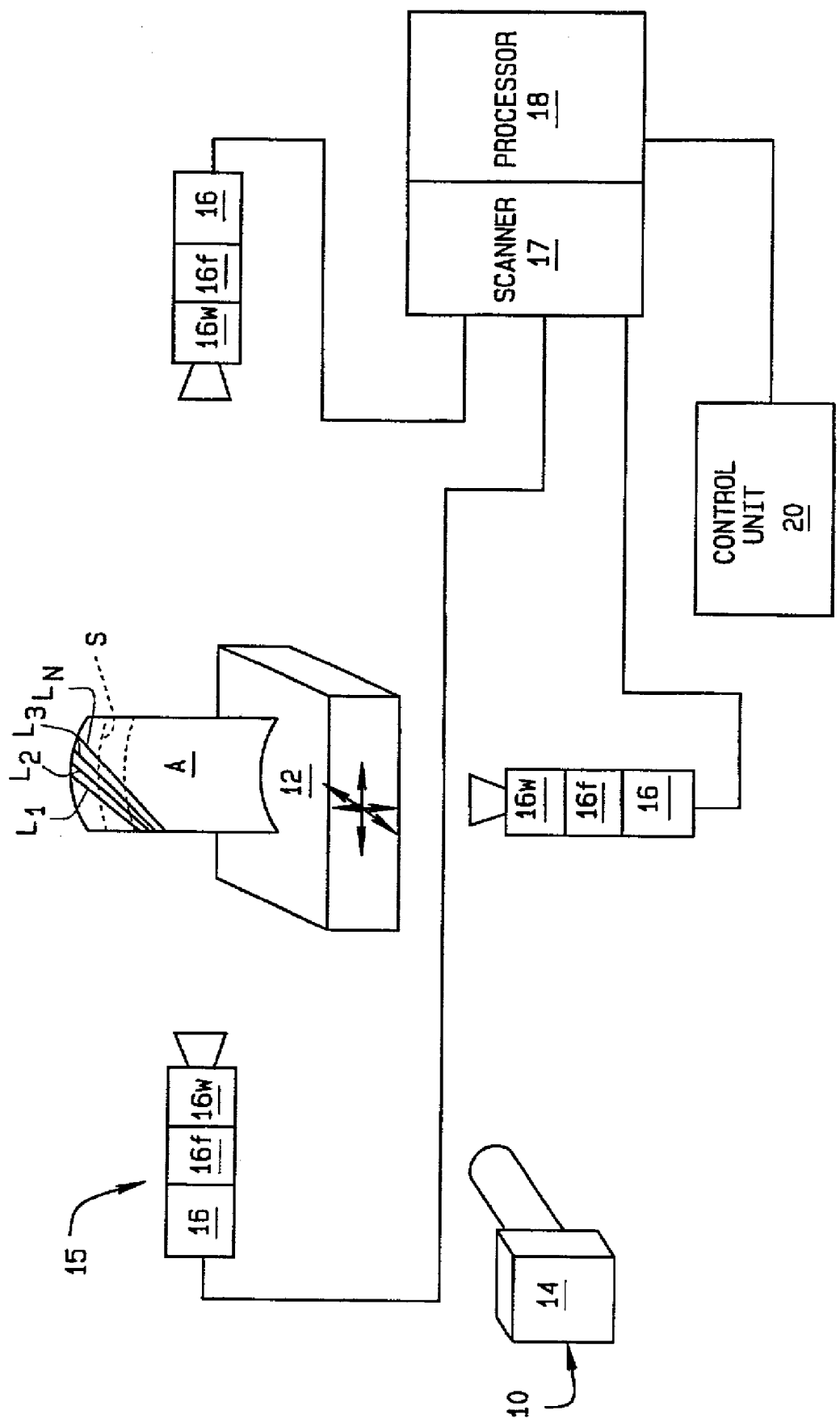
FIG. 1 is a simplified representation of a test setup for light gauge testing of a part.

Referring to FIG. 1, the test setup for a structured light system 10 used for light gauge testing of an airfoil A or similar part with a complex surface contour first includes a support or fixture 12 on which the airfoil is mounted. The fixture may be a movable fixture having six degrees of freedom so the part can be moved to any desired orientation. To test the part for acceptability, a laser light is projected onto the object from a laser light projector 14 and light reflections from the object are obtained using an imaging system 15. System 15 includes one or more cameras 16. These include windows 16w and polarizers 16p built into the imaging system, and associated electronics. Images obtained by the cameras are converted into digital images which are processed by a processor 18. The imaging system further includes a scanner 17. For purposes of determining acceptability of a part, the processor compares test data obtained from the part with corresponding data from a calibration artifact or the like. A control unit 20 is used to control the testing process.

As shown in FIG. 1, projector 14 illuminates the object with a series of light stripes indicated L1–Ln in the drawing. Those skilled in the art will understand that there may be more or fewer lines than those shown. Similarly, three cameras 16a–16c are shown in FIG. 1, the cameras being arrayed about the part to obtain images of the part from different angles. Again, the imaging system employed for viewing the object may utilize more of fewer cameras.

To obtain the most accurate data for analysis by processor 18. the test setup is calibrated prior to part testing, using a test specimen in place of a part A. This involves checking out each subsystem or component comprising the setup, as well as the overall setup. Environmental controls (not shown) are adjusted so the temperature and humidity with the test cell are within prescribed limits. The temperature and humidity are monitored throughout part testing and appropriate adjustments made to insure that these remain within limits.

The laser stripes projected onto the part should have consistent line width over the length of a test image evaluated to determine the quality of the image. Also important are the centeredness of the line, and light intensity across the width of the line. With respect to laser light projector 14, a critical factor is drift. Preferably, drift should be less than 0.25 mrad. Drift can be controlled by focusing output of the laser diode (a slab diode) at the object field (i.e., the section or area on the part which is being illuminated). Preferably, the diode is focused at a point approximately 1 meter beyond the part. In practice, the diode is first focused on at the part, and then the diode is rotated slightly to obtain a desired line width (as measured in mrads).

Achieving the desired focus can be achieved in a number of ways. One way, for example, is moving projector 14 closer to or further away from the test specimen mounted on the fixture. Or, fixture 12 may be adjusted to move the test specimen relative to projector 14. Another way involves obtaining a magnified view of the area at which the laser light is projected using a magnifying lens, for example. The magnifying lens has a reticle marked on the lens to measure focus size. In this procedure, the surface at which the laser light is directed is preferably a black surface. Another method is to use a video camera with no lens on it and pointed at the spot where the light is focused. A third method is to use a hand-held laser spot profiler.

Figure 2:
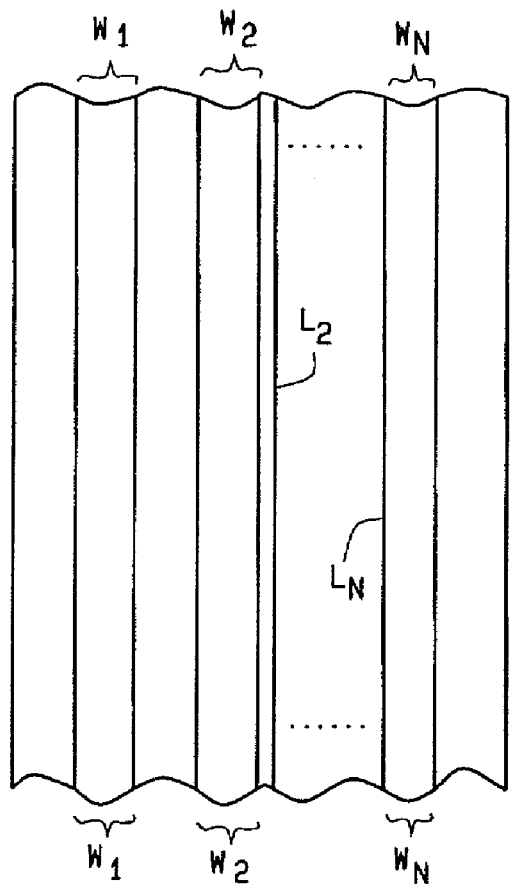
FIG. 2 illustrates the width of each line in a series of laser stripes projected at the part.

Regardless of the method employed, as shown in FIG. 2, the width of each line L1–Ln is shown for a defined section S of the test specimen (see FIG. 1). For each stripe or line, its width w1, w2, ... wn is measured along the length of the section. The width typically is between (X) and (Y) pixels and with the width of each line being substantially constant over section S. The width of the all the lines do not have to be the same, as shown in FIG. 2, but as a practical matter, all the lines will be substantially of the same width.

The center of each line L1–Ln preferably has a standard deviation of <0.07 pixels. With currently available lasers, noise effects on the line centers is on the order of 0.11 to 0.09 pixels. With a slab diode, noise is 0.06 pixels or less. Use of a slab diode in projector 14 has the advantages of lower noise, and higher power for use with polarizers. The higher power levels available also provide for better signals from the shinier portions of the part. To test for line centeredness and symmetry, an image of the illuminated test specimen is taken and converted into a digital format. The number of pixels comprising the width of the line is counted at different segments along the length of the line. A histogram is prepared and studied to find any asymmetrical elements, to perform standard deviations of a line at its center, and to take an average of the standard deviation calculated per 10 point segments. This latter is done to match light gauge testing operations.

Figure 3:
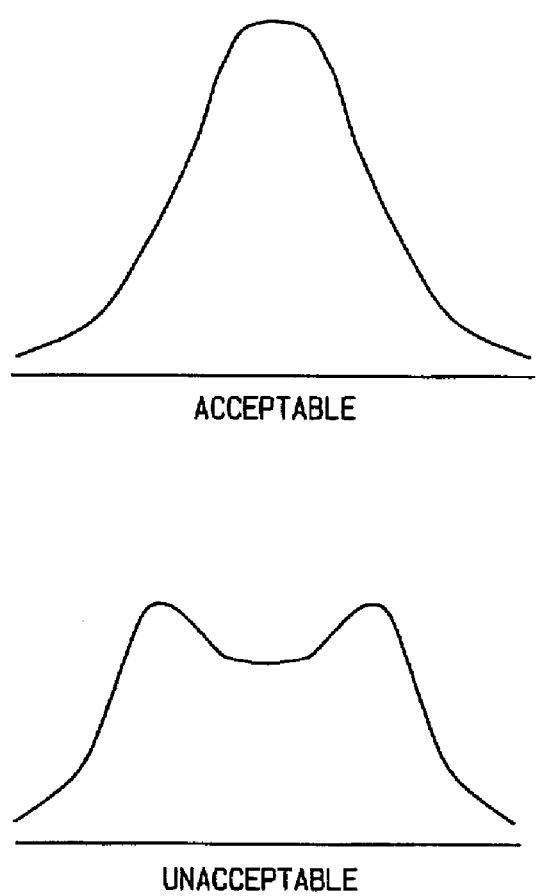
FIG. 3 is a series of graphs showing acceptable and unacceptable energy distribution patterns across the width of a laser stripe; and, FIG. 4 illustrates use of a calibrated illumination source to test a camera of the imaging system used in the test setup.

Next, as shown in FIG. 3, the intensity profile for each line is examined. To be acceptable, the profile should indicate a Gaussian distribution as indicated in the upper graph in the FIG. If the line is not properly projected onto the part, then a non-Gaussian intensity profile similar to that in the lower graph will result. If either the line width is not constant, or if the intensity profile is not Gaussian, then adjustments are made to the system and another calibration check is performed.

Once the desired focus (line width and intensity profile) is achieved, the laser is left on and the width of the lines is monitored for a predetermined period of time to determine if the width of the lines change (drift). In some circumstances, drift may be monitored for a period of a week or more.

Figure 4:
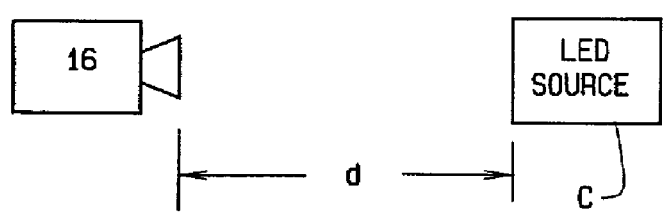

Next, the cameras 16 are typically commercially available cameras providing a signal-to-noise ratio on the order of 50–55 dB. They provide a capability of distinguishing between 100–125 Grey scale levels. As shown in FIG. 4, to test each camera, a calibrated illumination source C (an LED source, for example) is set a fixed distance d away from each camera 16 which views a Grey scale step scale. The resulting Grey scale output is now converted to a digital value, and the camera is adjusted to give the same level output for a given Grey scale value. Any variation in the amount of change seen for a step change from one Grey scale value to another will require an adjustment to the camera's gain, since the value should be constant for each step change in Grey scale level. After corrections and adjustments have been made, the cameras are checked for Grey scale values about 125 which is near the midpoint. The output value should be approximately 0.5 volts for this value. For a uniform area on the test specimen, variations in Grey scale values for that area should be within +/−1 level.

Occasionally, a distinctive ripple noise may be observed in a sensor during the alignment process. Previous experience has shown that the ripple is a uniform ripple seen by all the cameras 16, and the ripple is independent of the image. The source of the noise can be from the cameras, multiplexing boards (not shown), or associated electronics such as power supplies, etc. (also not shown). If ripple is observed, the simplest way of eliminating it is to switch out components one component (camera, boards, power supply) until the noise appears. Alternatively, the system can be tested using video test equipment.

With respect to optical components of the imaging system including the windows and polarizers, any deviation should be <1 wavelength per inch. To test the optical elements of the system, a transmitted wavefront can be tested by putting a collimated beam through a window/polarizer and using a shearing plate to observe wavefront error. Alternately, use of Ronchi rulings (one on the input, the other just behind the component) will show gross errors in the wavefront.

Scanner 17, which provides a despeckling function, drift should be <0.25 mrad, and alignment at 0.5 mrad. To effect proper alignment, real-time video feedback is used to view line width and symmetry of the reflected laser lines. This is done using a camera mounted on an alignment microscope, and viewing the image created by the standard 25 mm c-mount lens.

Heretofore, focusing of the cameras 16 has been done visually. The drawback with this is that it allows for a noticeable variation in magnification at the image. In accordance with the invention, the camera is now used to view a square pattern. As the camera is focused, the number of pixels from the edges of the pattern, at 75% of the viewing area of the camera is counted. The count should be within one pixel for all the cameras with the process is completed.

In summary, the present method is to insure proper alignment of a structured light system for use in light gauge measurements of part such as airfoils and turbine blades. Rather than using previous methods which primarily involved visual alignment of the test components with the article under test, what has been described is a structured process in which the respective components are individually checked to determine that they are functioning properly. After the individual components are tested and aligned, an overall system test is performed to verify that the integrated system is also functioning properly. Only then, is acceptance testing begun on individual parts.

In view of the foregoing, it will be seen that the several objects of the invention are achieved and other advantageous results are obtained. As various changes could be made in the above constructions without departing from the scope of the invention, it is intended that all matter contained in the above description or shown in the accompanying drawings shall be interpreted as illustrative and not in a limiting sense.

The invention claimed is:

1. In a testing procedure for light gauge testing of a part (A) in which a series of light stripes (L1–Ln) are projected onto the part by a structured light system, light reflected from the part being captured by an imaging system for evaluation, a method for setting up and aligning the respective components used in the testing procedure to obtain optimal information for evaluating acceptability of the part comprising:
    initially aligning a light projector and at least one camera of the imaging system with a test specimen of the object;
    projecting a series of light stripes (L1–Ln) onto the test specimen and capturing images of light reflections from the specimen;
    evaluating the images to determine characteristics of each light stripe;
    accepting the test setup and alignment if the characteristics of the light stripes are substantially uniform over a section (S) of the test specimen;
    but, modifying the test setup and alignment if any of the characteristics are not substantially uniform over the section; and
    testing parts (A) using the structured light system and imaging system after an acceptable test setup and alignment is achieved;
    wherein modifying the test setup and alignment includes repositioning the structured light system relative to the test specimen.

2. The method of claim 1 in which the test specimen (S) is mounted on a fixture, and modifying the test setup and alignment further includes reorienting the test specimen relative to the structured light system by adjusting or moving the fixture.

3. The method of claim 1 in which evaluating the images to determine characteristics of each light stripe (L1–Ln) includes determining the number of pixels extending across the width of a light stripe.

4. The method of claim 3 in which the number of pixels defining the width of a light stripe is between (X) pixels and (Y) pixels and is substantially constant along the length of the section (S) of the test specimen.

5. The method of claim 3 in which evaluating the images to determine characteristics of each light stripe (L1–Ln) further includes determining the center of each light stripe and the deviation in centeredness along the length of the section (S).

6. The method of claim 5 in which the center of each light stripe (L1–Ln) preferably has a standard deviation of <0.07 pixels along the length of the section (S).

7. The method of claim 3 in which evaluating the images to determine characteristics of each light stripe (L1–Ln) further includes determining the intensity distribution across the width of a light stripe.

8. The method of claim 7 in which the intensity distribution is a Gaussian distribution.

9. The method of claim 1 further including focusing each camera (16) used to capture images of the part (A) and light reflected off the part.

10. The method of claim 9 in which focusing each camera includes determining if the camera is capable of distinguishing between Grey scale levels within a range of such levels.

11. The method of claim 10 wherein focusing the camera includes setting a calibrated illumination source (C) a fixed distance (d) away from the camera and having the camera views the source.

12. The method of claim 11 in which the illumination source (C) is an LED source.

13. The method of claim 10 further including converting the image captured by the camera to a digital value, and adjusting the gain of the camera to provide a linear change in output for a given Grey scale value.

14. The method of claim 13 in which, after the camera gain is adjusted, the cameras are checked for Grey scale values about the midpoint of the range of Grey scale values observable by the camera.

15. The method of claim 1 in which optical components (16w, 16p) of the imaging system are tested to determine if there is any distortion.

16. The method of claim 15 in which the measured distortion should be <1 wavelength of distortion per inch.

17. The method of claim 15 in which the optical elements are tested by directing a collimated beam through a window/polarizer and using a shearing plate to measure any distortion.

18. The method of claim 1 in which the temperature and humidity of the test facility is controlled to provide an optimal testing environment in which performance of the various testing components is not effected by extremes of either.

19. In a testing procedure for light gauge testing of a part (A) in which a series of light stripes (L1–Ln) are projected onto the part by a structured light system, light reflected from the part being captured by an imaging system for evaluation, a method for setting up and aligning the respective components of used in the testing procedure to obtain optimal information for evaluating acceptability of the part comprising:
    initially aligning a light projector (14) and at least one camera of the imaging system with a test specimen of the object;
    projecting a series of light stripes (L1–Ln) onto the test specimen and capturing images of light reflections from the specimen;
    evaluating the images to determine characteristics of each light stripe including determining the number of pixels extending across the width of a light stripe, the center of each light stripe and the deviation in centeredness along the length of the section (S), and the intensity distribution across the width of a light stripe;
    focusing each camera used to capture images of the part (A) and light reflected off the part, including determining if the camera can distinguish between each Grey scale level within a range of such levels;
    testing optical components of the imaging system to determine if there is any distortion present;
    accepting the test setup and alignment if the characteristics of the light stripes are substantially uniform over a section (S) of the test specimen, each camera in the imaging system is focused, and any measured distortion is substantially eliminated; and testing parts (A) using the structured light system and imaging system after an acceptable test setup and alignment is achieved;

wherein modifying the test setup and alignment includes repositioning the structured light system relative to the test specimen.

20. The method of claim 19 in which the number of pixels defining the width of a light stripe is between (X) pixels and (Y) pixels and is substantially constant along the length of the section (S) of the test specimen, the center of each light stripe (L1–Ln) has a standard deviation of <0.07 pixels along the length of the section (S), and which the intensity distribution is a Gaussian distribution.

21. The method of claim 20 in which focusing each camera (16) includes determining if the camera is capable of distinguishing between Grey scale levels within a range of such levels.

22. The method of claim 21 wherein focusing the camera includes setting a calibrated illumination source (C) a fixed distance (d) away from the camera and having the camera views the source.

23. The method of claim 22 further including converting the image captured by the camera to a digital value, and adjusting the gain of the camera to provide a linear change in output for a given Grey scale value.

24. The method of claim 21 in which the measured distortion of the optical elements of the imaging system should be <1 wavelength of distortion per inch, the optical elements are tested by directing a collimated beam through a window/polarizer and using a shearing plate to measure any distortion.

25. The method of claim 24 further including focusing each camera used to capture images of the part (A) and light reflected off the part, including determining if the camera can distinguish between each Grey scale level within a range of such levels, and testing optical components of the imaging system to determine if there is any distortion present.

26. The method of claim 19 in which the temperature and humidity of the test facility is controlled to provide an optimal testing environment in which performance of the various testing components is not effected by extremes of either.

27. In a testing procedure for light gauge testing of a part (A) in which a series of light stripes (L1–Ln) are projected onto the part by a structured light system (14), light reflected from the part being captured by an imaging system for evaluation, a method for setting up and aligning the respective components of used in the testing procedure to obtain optimal information for evaluating acceptability of the part comprising:

initially aligning a light projector and at least one camera of the imaging system with a test specimen of the object;

projecting a series of light stripes (L1–Ln) onto the test specimen and capturing images of light reflections from the specimen;

evaluating the images to determine characteristics of each light stripe including determining the number of pixels extending across the width of a light stripe, the center of each light stripe and the deviation in centeredness along the length of the section (S), and the intensity distribution across the width of a light stripe;

accepting the test setup and alignment if the characteristics of the light stripes are substantially uniform over a section (S) of the test specimen;

but, modifying the test setup and alignment if any of the characteristics are not substantially uniform over the section; and testing parts (A) using the structured light system and imaging system after an acceptable test setup and alignment is achieved;

wherein modifying the test setup and alignment includes repositioning the structured light system relative to the test specimen.

* * * * *

UNITED STATES PATENT AND TRADEMARK OFFICE
CERTIFICATE OF CORRECTION

PATENT NO. : 7,206,717 B2  
APPLICATION NO. : 10/063787  
DATED : April 17, 2007  
INVENTOR(S) : Harding Page 1 of 1

It is certified that error appears in the above-identified patent and that said Letters Patent is hereby corrected as shown below:

On the Title Page

Item (75), under "Inventor", Line 3, delete "Hardy" and insert -- Harding --, therefor.

In Column 2, Line 62, delete "18. the" and insert -- 18, the --, therefor.

In Column 6, Line 41, in Claim 19, after "components" delete "of".

In Column 8, Line 9, in Claim 27, after "components" delete "of".

Signed and Sealed this  
Seventh Day of February, 2012

David J. Kappos  
*Director of the United States Patent and Trademark Office*